(12) United States Patent
Lin et al.

(10) Patent No.: US 10,683,487 B2
(45) Date of Patent: Jun. 16, 2020

(54) *MYRMECRIDIUM FLEXUOSUM* **NUK-21, NOVEL LACTOSE OXIDASE ISOLATED FROM *MYRMECRIDIUM FLEXUOSUM* NUK-21, AND METHOD FOR CONVERSION OF LACTOSE INTO LACTOBIONIC ACID BY NOVEL LACTOSE OXIDASE**

(71) Applicant: NATIONAL UNIVERSITY OF KAOHSIUNG, Kaohsiung (TW)

(72) Inventors: Shuen-Fuh Lin, Kaohsiung (TW); Cheng-Ke Li, Kaohsiung (TW); Yi-Pei Chung, Kaohsiung (TW)

(73) Assignee: National University of Kaohsiung, Kaohsiung (TW)

( * ) Notice: Subject to any disclaimer, the term of this patent is extended or adjusted under 35 U.S.C. 154(b) by 0 days.

(21) Appl. No.: 16/120,868

(22) Filed: Sep. 4, 2018

(65) Prior Publication Data
US 2019/0127709 A1   May 2, 2019

(30) Foreign Application Priority Data
Nov. 2, 2017   (TW) .............................. 106137947 A (51) Int. Cl.
| | | |
|---|---|---|
| *C12N 9/04* | (2006.01) | |
| *C12N 1/14* | (2006.01) | |
| *C12R 1/645* | (2006.01) | |
| *C12P 19/12* | (2006.01) | |

(52) U.S. Cl.
CPC ............. *C12N 9/0006* (2013.01); *C12N 1/14* (2013.01); *C12P 19/12* (2013.01); *C12R 1/645* (2013.01); *C12Y 101/03* (2013.01)

(58) Field of Classification Search
CPC ...... C12N 1/14; C12N 9/0006; C12Y 101/03; C12R 1/645; C12P 19/12
See application file for complete search history.

(56) References Cited

PUBLICATIONS

Lin et al., Identification of a novel lactose oxidase in Myrmecridium flexuosum NUK-21. FEBS Openbio., 2019, vol. 9: 364-373. (Year: 2019).*

* cited by examiner

*Primary Examiner* — Ganapathirama Raghu
(74) *Attorney, Agent, or Firm* — Rosenberg, Klein & Lee (57) ABSTRACT

A *Myrmecridium flexuosum* NUK-21, a novel lactose oxidase isolated from the *Myrmecridium flexuosum* NUK-21 and a method for conversion of lactose into lactobionic acid (LBA) by the novel lactose oxidase are disclosed herein. The *Myrmecridium flexuosum* NUK-21 produces high yields of the novel lactose oxidase and the novel lactose oxidase has higher reactivity and specificity of converting lactose into lactobionic acid.

6 Claims, 11 Drawing Sheets
(5 of 11 Drawing Sheet(s) Filed in Color)

Specification includes a Sequence Listing.

A: 2.5% lactobionic acid (1 μl)
B: product (2 μl)

SEQUENCE LISTING

```
<160> NUMBER OF SEQ ID NOS: 1

<210> SEQ ID NO 1
<211> LENGTH: 554
<212> TYPE: DNA
<213> ORGANISM: Myrmecridium flexuosum
<220> FEATURE:
<223> OTHER INFORMATION: rDNA ITS1-5.8S-ITS2

<400> SEQUENCE: 1
aagtcgtaac aaggtctccg ttggtgaacc agcggaggga tcattacgag agtgtcacca      60
ctcccaaccc attgtttacc tacccgtcca ccgtgcttcg gcaggcagcc ctgtgggaca     120
gagcctcgcc cccctccgcg gggggtgcct gccgctggcc aaccaacaac tctagctgtt     180
ttagtaccat ctgagtcttc cacaaatgaa caaaactttc aacaacggat ctcttggttc     240
tggcatcgat gaagaacgca gcgaaatgcg ataagtaatg tgaattgcag aattcagtga     300
atcatcgaat ctttgaacgc acattgcgcc cactagtatt ctggtgggca tgcctgttcg     360
agcgtcattt caaccctcaa gcctggcttg gtgttggggc tctgcgcaac gcagtccctt     420
aaattcagtg gcggacacgc taggtctccg agcgcagtag tttcttctcg cttcgggcgt     480
```

```
ccggcgtggg cttgcctcgc acccaacttc tcaaggttga cctcggatca ggtaggaata      540
cccgctgaac ttaa                                                        554
```

MYRMECRIDIUM FLEXUOSUM NUK-21, NOVEL LACTOSE OXIDASE ISOLATED FROM MYRMECRIDIUM FLEXUOSUM NUK-21, AND METHOD FOR CONVERSION OF LACTOSE INTO LACTOBIONIC ACID BY NOVEL LACTOSE OXIDASE

BACKGROUND OF THE INVENTION

1. Field of the Invention

The present invention relates to a *Myrmecridium flexuosum* NUK-21, a novel lactose oxidase isolated from the *Myrmecridium flexuosum* NUK-21 and a method for conversion of lactose into lactobionic acid (LBA) by the novel lactose oxidase, especially for a novel lactose oxidase isolated from the *M. flexuosum* NUK-21 deposited under the DSMZ deposit accession number DSM 32781, which possess high substrate specificity, high catalytic rate and high lactose conversion rate.

2. Description of Related Art

Lactobionic acid is a high-value lactose derivative to be applied in the food cosmetics, medicine and industry. In the early years, almost no suitable strain and enzyme can be used to produce lactobionic acid, so most of lactobionic acids were produced by chemical transformation, for instance, oxidation of lactose by bromine in an aqueous buffered solution to produce lactobionic acid products (Carbohydr Res. 2005; 340:2698-705). However, this method also generates toxic by-products and causes environmental pollution.

Microbial production of lactobionic acid is a method of using fermentation tank to conduct microbial fermentation and produce large quantities of lactobionic acid. It is known that the strains capable of fermenting lactobionic acid includes *Pseudomonas taetrolens* (Bioresour Technol. 2011; 102:9730-6; Bioresour Technol. 2012; 109:140-7; Bioresour Technol. 2013; 134:134-42), *Zymomonas mobilis* (Adsorption 2010; 17:145-158; J Ind Microbiol Biotechnol, 2013; 40:1-10), *Burkholderia cepacia* (European Patent Application Pub. No.: EP19900200393; 1990; J Applied Glycoscience, 2003; 50:117-120; J of Applied Glycoscience, 2006; 53:7-11), *Acetobacter orientalis* (Bioscience, biotechnology, and biochemistry, 2012; 76:361-3) and the like. However, some high-yielding strains are mutant strains which may cause safety concerns. Besides, although the fermentation process of the above-mentioned microorganisms can produce a fermentation broth containing lactobionic acid in a fermentation tank, the subsequent purification is difficult to conduct. Therefore, a method for enzyme production is proposed.

The method of enzyme production includes using specific enzymes to conduct a series of reactions, e.g. lactose oxidation, so as to produce oxidize lactose. The advantage of the enzyme catalytic method is that the relatively pure lactose can be directly converted into lactobionic acid, so the purification steps after the reactions is substantially simplified or can be removed. Compared with the microbial fermentation method, the enzyme catalytic method obtains high purity of lactobionic acid in a cheaper way. However, lactobionic acid production of the enzyme catalytic method cannot be mass-produced in a fermenter due to its complicated steps including culturing a strain to produce desired enzymes, isolating and purifying the desired enzymes, reacting the enzymes with a lactose-containing medium, ultrafiltering the lactose-containing medium to separate macromolecules and small molecules, and finally conducting column purification to obtain lactobionic acid with the desired purity.

In recent years, some enzymes more suitable for industrial application have been developed. For instance, LactoYIELD®, a novel carbohydrate:acceptor oxidoreductase from *Microdochium nivale*, is designed to convert lactose into lactobionic acid by Chr. Hansen and Novozymes (Eur J Biochem. 2001 February; 268:1136-42). Differ from cellobiose dehydrogenases that need cofactors as electron acceptors, the LactoYIELD® can use dissolved oxygen as electron acceptors, so the production costs of lactobionic acid can be significantly reduced. Furthermore, the study shows that the substrate specificity of the enzyme produced by the original strain for lactose is only 52% (100% specificity for cellobiose). After the enzyme is transformed to other strains for expression, the substrate specificity for lactose is decreased from 52% to 28% (100% specificity to cellobiose). The phenomenon may be caused by the reduction of the original strain or the generation of toxicity in transgenic strains.

A patent number CN 1976593 B, issued on 27 Mar. 2013, and a patent number US 20070105200 A1 published on 10 May 2007, both disclosed an enzymatic process for obtaining increased yield of lactobionic acid. The carbohydrate oxidase for converting lactose into lactobionic acid is obtained from *Microdochium nivale*. However, the carbohydrate oxidase must be added with catalase to increase the conversion rate of lactose into lactobionic acid due to its low conversion efficiency to lactobionic acid.

SUMMARY OF THE INVENTION

In order to efficiently produce lactobionic acid, strains with high yields and oxidative enzymes with high reactivity and high specificity are needed.

The primary object of the present invention is to provide a *Myrmecridium flexuosum* NUK-21, a novel lactose oxidase isolated from the *Myrmecridium flexuosum* NUK-21 and a method for conversion of lactose into lactobionic acid by the novel lactose oxidase, especially for a novel lactose oxidase isolated from the *M. flexuosum* NUK-21 deposited under the DSMZ deposit accession number DSM 32781. The novel lactose oxidase with high substrate specificity, high catalytic rate and high lactose conversion rate can be used to efficiently produce lactobionic acids.

Disclosed herein is an isolated and purified *Myrmecridium flexuosum* NUK-21, deposited under the DSMZ deposit accession number DSM 32781.

Disclosed herein is a process for preparation of a *Myrmecridium flexuosum* NUK-21 culture, comprising inoculating a culturing medium with an isolate of *Myrmecridium flexuosum* NUK-21 and culturing the *Myrmecridium flexuosum* NUK-21 isolate in the culturing medium to obtain a *Myrmecridium flexuosum* NUK-21 culture.

Disclosed herein is a novel lactose oxidase isolated from the *Myrmecridium flexuosum* NUK-21. The novel lactose oxidase contains zinc ion ($Zn^{2+}$) as a coenzyme and has a molecular weight of 47.2 kDa, a catalytic reaction rate for lactose (Km) of 0.076 mM, a catalyst rate constant ($K_{cat}$) of 97.1 $s^{-1}$, and a conversion rate of 100% for lactose.

According to an embodiment of the present invention, the culturing medium is selected from a solid medium containing wheat bran and water, a liquid medium containing wheat bran, sodium chloride (NaCl), and cupric ions ($Cu^{2+}$), or a liquid medium containing defatted soybean flours. Preferably, the culturing medium is a solid-state fermentation (SSF) medium containing wheat bran and water at a ratio of 1:1.5 to 1:2.5, or a submerged fermentation (SmF) liquid medium added with wheat brans or defatted soybean flours to extracellularly generate the novel lactose oxidase. Furthermore, the SmF liquid medium added with wheat brans is preferably added with 0.5% sodium chloride (NaCl) and 0.01% cupric ions (such as copper sulfate) to reach a higher enzyme activity.

According to an embodiment of the present invention, the solid medium in which the isolated and purified *Myrmecridium flexuosum* NUK-21 is cultured for 3.5 days has an enzyme activity of 6 units/g, and the liquid medium in which the isolated and purified *Myrmecridium flexuosum* NUK-21 is cultured for 4 days has an enzyme activity of 0.55 unit/ml.

According to an embodiment of the present invention, the culturing medium inoculated with the *Myrmecridium flexuosum* NUK-21 isolate is cultured at a temperature ranging from 25° C. to 35° C. for 3 to 7 days.

Compared with the technique available now, the *Myrmecridium flexuosum* NUK-21 of the present invention has a high yielding rate (5 g of wheat brans producing more than 25 units of lactose oxidase), high substrate specificity, high catalytic rate, and high lactose conversion rate. Therefore, the production of lactobionic acid using the *Myrmecridium flexuosum* NUK-21 has the advantage of low cost.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

An isolated and purified *Myrmecridium flexuosum* NUK-21, deposited under the DSMZ deposit accession number DSM 32781, is disclosed herein.

A process for preparation of a *Myrmecridium flexuosum* NUK-21 culture is also disclosed herein. It comprises inoculating a culturing medium with an isolate of *Myrmecridium flexuosum* NUK-21 and culturing the *Myrmecridium flexuosum* NUK-21 isolate in the culturing medium to obtain a *Myrmecridium flexuosum* NUK-21 culture. A novel lactose oxidase is further isolated from the NUK-21 culture. Preferably, the culturing medium is selected from a solid medium containing wheat bran and water, a liquid medium containing wheat bran, sodium chloride (NaCl), and cupric ions ($Cu^{2+}$), or a liquid medium containing defatted soybean flours. For instance, the culturing medium is a solid-state fermentation (SSF) medium containing wheat bran and water at a ratio of 1:1.5 to 1:2.5, or a submerged fermentation (SmF) liquid medium added with wheat brans or defatted soybean flours to extracellularly generate the novel lactose oxidase. Preferably, the culturing medium inoculated with the *Myrmecridium flexuosum* NUK-21 isolate is cultured at a temperature ranging from 25° C. to 35° C. for 3 to 7 days. Furthermore, the SmF liquid medium added with wheat brans is preferably added with 0.5% sodium chloride (NaCl) and 0.01% cupric ions (such as copper sulfate) to reach a higher enzyme activity.

A novel lactose oxidase isolated from the *Myrmecridium flexuosum* NUK-21 disclosed herein contains a zinc ion as a coenzyme and has a molecular weight of 47.2 kDa, a catalytic reaction rate for lactose (Km) of 0.076 mM, a catalyst rate constant ($K_{cat}$) of 97.1 $s^{-1}$, and a conversion rate of 100% for lactose.

A method for production of a novel lactose oxidase is also disclosed herein. It comprises (a) inoculating a culturing medium with a *Myrmecridium flexuosum* NUK-21; and (b) culturing the *Myrmecridium flexuosum* NUK-21 at a temperature of 25° C. to 35° C. for 3 to 7 days to obtain the novel lactose oxidase. The *Myrmecridium flexuosum* NUK-21 is deposited under the DSMZ deposit accession number DSM 32781. Preferably, the culturing medium is selected from a solid medium containing wheat bran and water, a liquid medium containing wheat bran, sodium chloride (NaCl), and cupric ions ($Cu^{2+}$), or a liquid medium containing defatted soybean flours. For instance, the culturing medium is a solid-state fermentation (SSF) medium containing wheat bran and water at a ratio of 1:1.5 to 1:2.5, or a submerged fermentation (SmF) liquid medium added with wheat brans or defatted soybean flours to extracellularly generate the novel lactose oxidase. Preferably, the culturing medium inoculated with the *Myrmecridium flexuosum* NUK-21 isolate is cultured at a temperature ranging from 25° C. to 35° C. for 3 to 7 days. Furthermore, the SmF liquid medium added with wheat brans is preferably added with 0.5% sodium chloride (NaCl) and 0.01% cupric ions (such as copper sulfate) to reach a higher enzyme activity.

A method for conversion of lactose into lactobionic acid by a novel lactose oxidase, is also disclosed herein. It comprises inoculating a culturing medium with the isolated and purified *Myrmecridium flexuosum* NUK-21 as claimed in claim 1, and culturing the isolated and purified *Myrmecridium flexuosum* NUK-21 under a culturing condition to convert lactose into lactobionic acid. Preferably, the culturing medium is selected from a solid medium containing wheat bran and water, a liquid medium containing wheat bran, sodium chloride (NaCl), and cupric ions ($Cu^{2+}$), or a liquid medium containing defatted soybean flours. For instance, the culturing medium is a solid-state fermentation (SSF) medium containing wheat bran and water at a ratio of 1:1.5 to 1:2.5, or a submerged fermentation (SmF) liquid medium added with wheat brans or defatted soybean flours to extracellularly generate the novel lactose oxidase. Furthermore, the SmF liquid medium added with wheat brans is preferably added with 0.5% sodium chloride (NaCl) and 0.01% cupric ions (such as copper sulfate) to reach a higher enzyme activity. More preferably, the solid-state fermentation (SSF) medium in which the isolated and purified *Myrmecridium flexuosum* NUK-21 is cultured for 3.5 days has an enzyme activity of 6 units/g, and the submerged fermentation (SmF) liquid medium in which the isolated and purified *Myrmecridium flexuosum* NUK-21 is cultured for 4 days has an enzyme activity of 0.55 unit/ml.

Hereinafter, an exemplary embodiment of the present invention will be described in detail with reference to the accompanying drawings.

Figure 1:
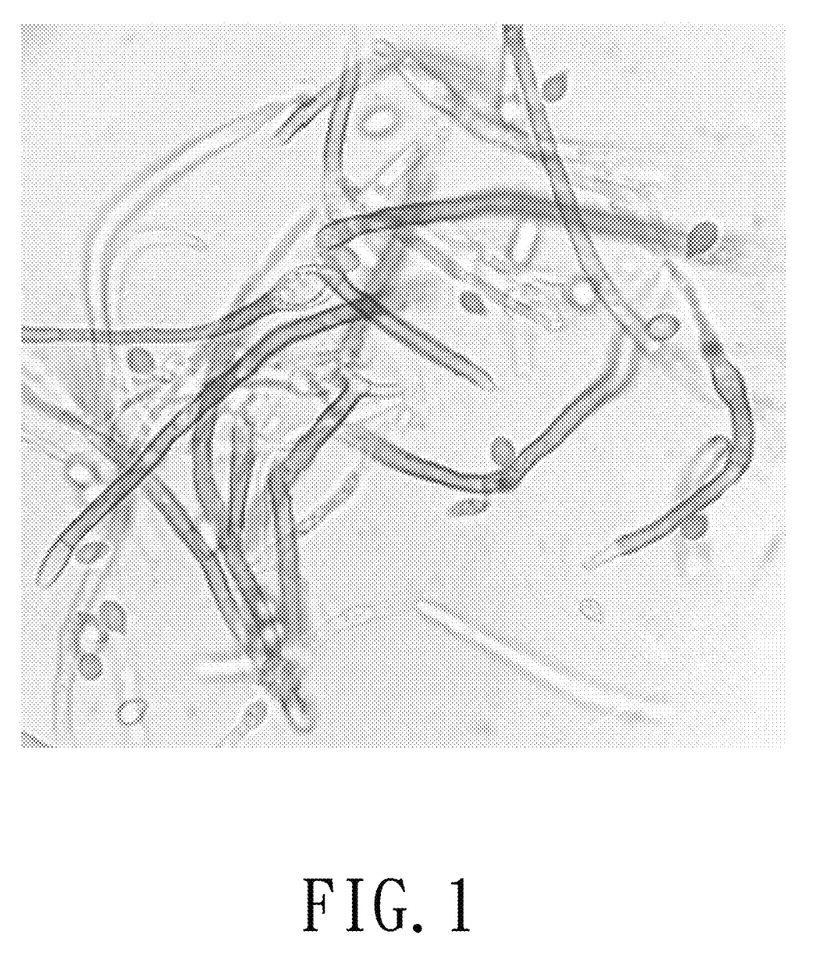
FIG. 1 shows a representative diagram of a *Myrmecridium flexuosum* NUK-21 strain according to the present invention.

Briefly, a fungal strain (*Myrmecridium flexuosum* NUK-21) capable of producing lactose oxidase was isolated from soil. The fungal strain was named as *Myrmecridium flexuosum* NUK-21 (referred to as NUK-21 strain) and deposited under the DSMZ deposit accession number DSM 32781. The NUK-21 strain was cultured in a malt extract agar (MEA) medium at a temperature of 25° C. for 13 days and then observed under an optical microscope (NIKON ECLIPSE E100) as shown in FIG. 1, by 400× magnification. The color of the colony was pale orange to orange, and the colony was covered with spores in the center. The conidiophore stalks had no branch and straight or twisted shapes, thick-walled, and transverse septum. Sporozoites were formed on the conidiophore stalks and had cylindrical, straight or twisted shapes, variable length, translucent to light brown color, and scattered pimple-shaped small teeth. Conidia were solitary, transparent, thin-walled, no septum, and with smooth or finely wart appearance, oval or fusiform shape and a size of 3.4-8.6×2.5-4.7 µm. The rDNA ITS1-5.8S-ITS2 sequence (554 bp) is represented by SEQ ID NO: 1. The partial sequence of rDNA ITS1-5.8S-ITS2 was analyzed and compared with the data on the NCBI GenBank database and with reference to the classification literature. The results showed that the strain of the present invention was closest to *Myrmecridium flexuosum* and *Myrmecridium schulzeri*; the sequence identities with *M. flexuosum* CBS 398.76 (EU041768) is 97.76% (479/490), and the sequence identity with *M. schulzeri* is 100% (488/488)–95.09% (465/489). Finally, according to the characteristics of colony and microstructure and the results of the sequence alignment of rDNA ITS1-5.8S-ITS2 fragment, NUK-21 strain was identified as *Myrmecridium flexuosum*.

Experiment 1: Strain Culture and Enzyme Production (1) Strain Culture

A NUK-21 strain was inoculated in a MY plate medium (containing 0.3% malt extract, 0.3% yeast extract, 0.5% peptone, 1% glucose, and 1.5% agar) at 30° C. for 3-5 days. Afterwards, 2×2 cm of fungi grown in the plate medium were cut out for inoculation into a 250-ml triangular conical flask containing 5 g of wheat bran mixed with water and cultured at 30° C. for 3-5 days. After the hyphae were covered on the surface of wheat bran, 50 ml of 50 mM Tris-HCl buffer (pH 7.8) (A buffer) containing 0.2% SDS was added for enzyme extraction. The residual wheat bran was filtrated by a gauze and the filtrate was centrifuged at 12,000×g at 4° C. for 5 minutes to remove the fungi pellet. The supernatant enzyme solution was obtained and the oxidase activity was determined by peroxidase chromogen method with lactose as the substrate.

(2) Solid-State Fermentation (SSF)

A NUK-21 strain was cultured in a medium containing five grains of wheat bran and different amounts of water at 30° C. for 3.5 days. As a result, it was found that when cultured on a solid medium added with 7.5 to 12.5 ml of water, lactose oxidase having a higher activity was produced, about 6 units of lactose oxidase activity per gram of wheat bran medium.

(3) Analysis of Time Course of Enzyme Production in Solid-State Fermentation (SSF)

A NUK-21 strain was cultured in a medium containing five grams of wheat bran and 10 ml of water at 30° C. for 2-7 days. The medium was taken out at different culturing days and extracted by 50 ml of A buffer containing 0.2% SDS. Then, the enzyme activity of lactose oxidase was measured.

Figure 2:
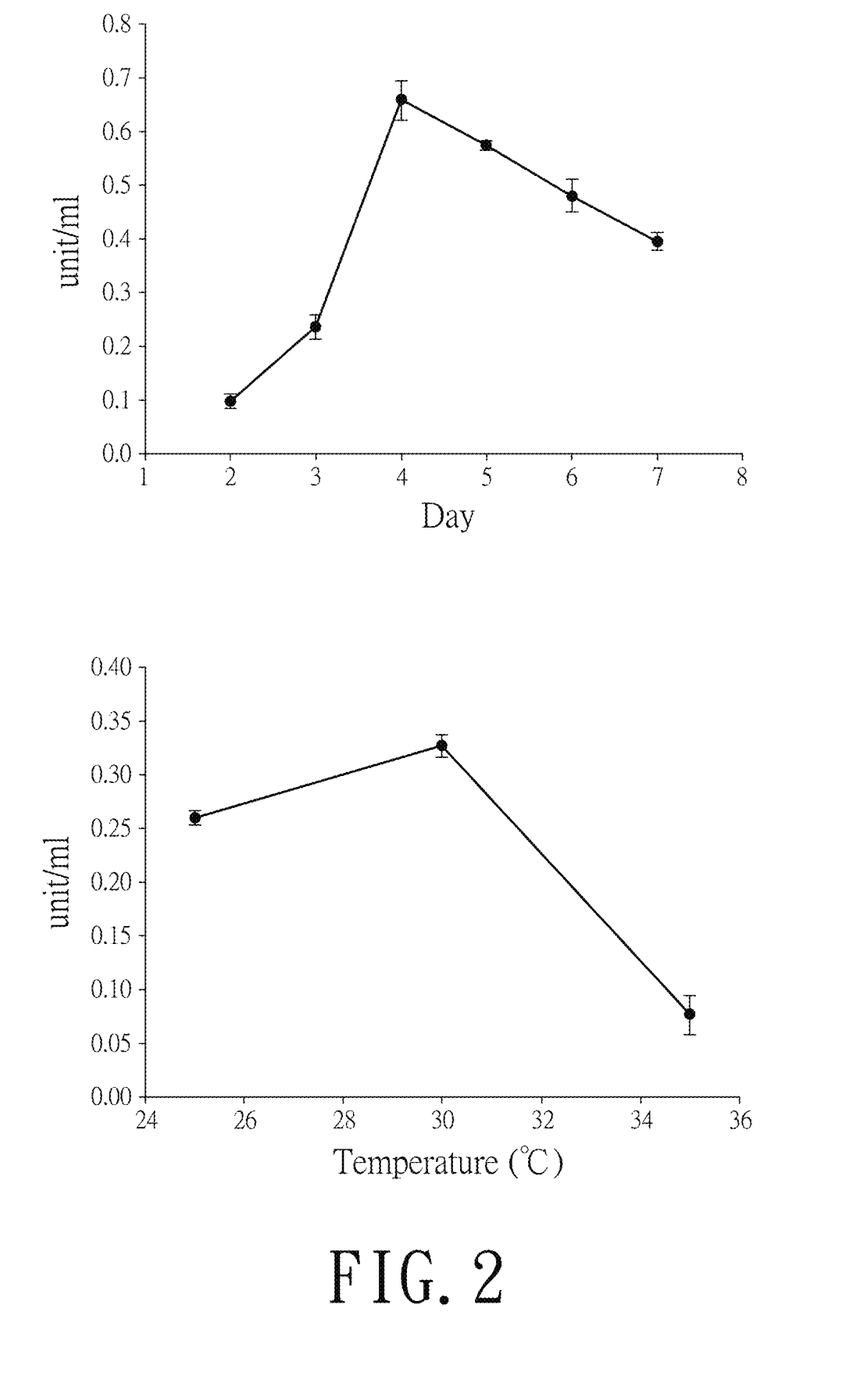
FIG. 2 shows effects of culturing day and temperature on production of a novel lactose oxidase according to the present invention.

Referring to FIG. 2, the lactose oxidase activity was low on the second day and increased on the third day. On the fourth day, lactose oxidase reached the highest activity. From the culture flask of the third day, it was found that the wheat bran was covered with tiny gray hyphae, and the wheat bran color also turned from yellow brown to dark brown. The optimal culturing time for production of the lactose oxidase is four days. Furthermore, NUK-21 strain was preferably cultured in the medium containing five grams of wheat bran and 10 ml of water at about 30° C. At 35° C., only 23% of enzyme activity remained in the extract.

(4) Submerged Fermentation (SmF)

For submerged fermentation (SmF) production, the basal medium containing 0.5% NaCl, 0.2% $K_2HPO_4$, and 0.02% $MgSO_4 \cdot 7H_2O$ was used for optimum production. Various carbon or nitrogen sources as shown in Table 1 were respectively added into 250-mL flasks for fermentation at 30° C. for 7 days on a rotary shaker at 130 rpm. The culture broth was filtered through 3 or 4 layers of muslin cloth, and the filtrate was centrifuged at 12,000×g at 4° C. for 20 min. The cell-free supernatant recognized as the crude enzyme extract was determined by peroxidase chromogen method and used for subsequent assays. Among the different organic sources, the defatted soybean flour and the wheat bran were preferable choices of additives for enzyme production. NUK-21 strain cultured in the medium containing the defatted soybean flour or the wheat bran has increased activity and production of lactose oxidase compared with other kinds of sources.

TABLE 1

Effect of organic sources on the production of lactose oxidase from the NUK-21 strain in submerged fermentation

| Additives (4%) | Enzyme activity (unit/ml) | Protein (ml/mg) |
|---|---|---|
| Bran coat | 0 | — |
| Rice bran | 0 | — |
| Defatted soybean flour | 0.22 ± 0.05 | 4.7 |
| Wheat bran | 0.18 ± 0.04 | 2.3 |
| Corn flour | 0 | — |
| Millet | 0 | — |

The optimal production conditions of the defatted soybean flour and the wheat bran were discussed respectively. The most suitable liquid culture condition for the NUK-21 strain was also determined by the choice of nitrogen sources and concentration, the optimum culture temperature, pH value, NaCl, surfactant and different metal ions, to provide a scale-up fermentation.

Figure 3:
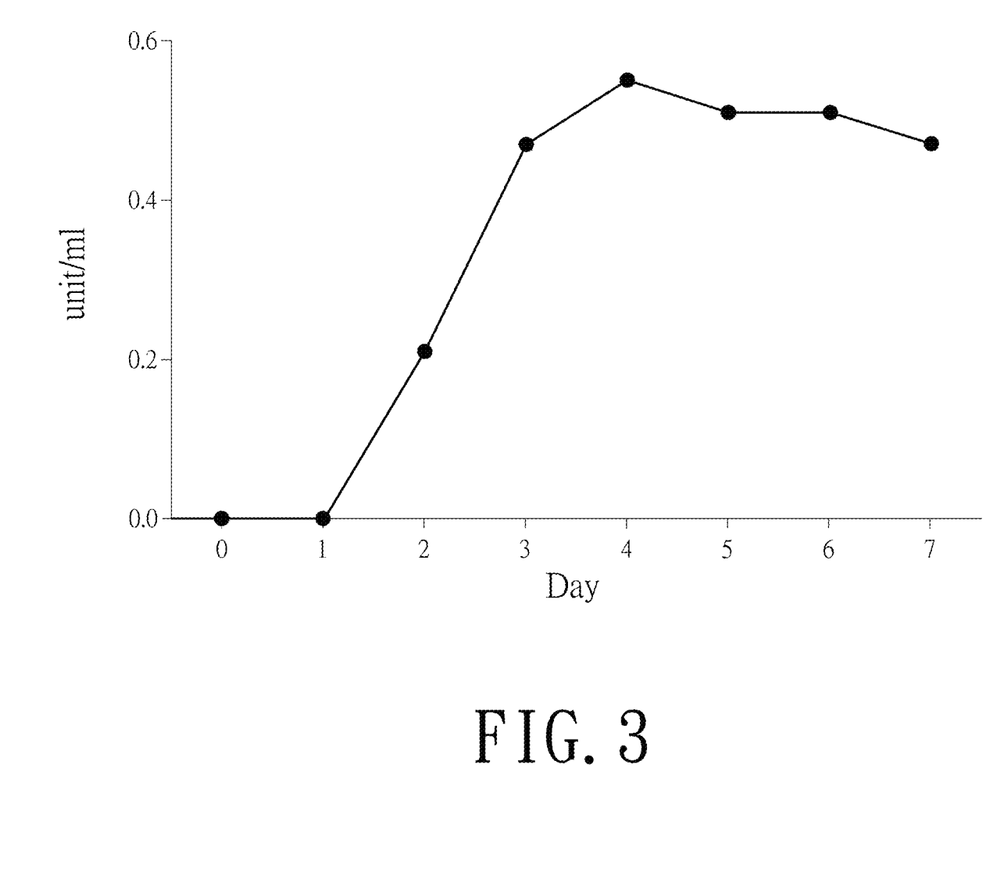
FIG. 3 shows a time-variation analysis of production of lactose oxidase of the NUK-21 cultured in a liquid medium containing defatted soybean flours according to the present invention.

It was found that the presence or absence of NaCl in defatted soybean flour had a great influence on submerged fermentation and the enzyme activity of lactobionic acid without NaCl was significantly increased. Furthermore, as shown in FIG. 3, up to 0.55 unit/ml of enzyme yield was obtained when the NUK-21 strain was cultured in a 250-ml flask with a 50 ml medium containing 4% defatted soybean flour, 1% cellulose, 0.2% $K_2HPO_4$, and 0.02% $MgSO_4$ at 30° C. for 4 days on a rotary shaker at 130 rpm.

In the wheat bran-containing medium, it was found that the effect of NaCl on submerged fermentation was not significant, but the effect of the metal ions on the liquid culture was significant. In measuring the effect of metal ions on production of lactose oxidase from the NUK-21 strain, the NUK-21 strain was cultured in a basal medium containing 4% wheat bran, 0.5% NaCl, 0.2% $K_2HPO_4$, 0.02% $MgSO_4$, and 0.01% of different metal ions at 30° C. for 4 days on a rotary shaker at 130 rpm.

As shown in Table 2, some metal ions increased the enzyme activity by about two folds compared with the control group (blank group). The group added with 0.01% cupric ions ($Cu^{2+}$) showed the highest enzyme activity of 0.61 unit/ml.

TABLE 2

Effect of various metal ions on the production of lactose oxidase from the NUK-21 strain in submerged fermentation

| Metal ions (0.01%) | Enzyme activity (unit/ml) |
|---|---|
| Control | 0.23 |
| $CuSO_4$ | 0.61 |
| $CdSO_4$ | 0.42 |
| $K_2SO_4$ | 0.26 |
| $Fe_2(SO_4)_3$ | 0.25 |
| $Z_nSO_4$ | 0.22 |
| $Na_2SO_4$ | 0.26 |
| $MnSO_4$ | 0.37 |
| $Al_2(SO_4)_3$ | 0.37 |
| $NiCl_2$ | 0.43 |
| $CaCl_2$ | 0.20 |
| $FeCl_3$ | 0.27 |
| $CoCl_2$ | 0.26 |
| $PbCl_2$ | 0.29 |
| $SnCl_4$ | 0.32 |
| $HgCl_2$ | 0.02 |
| $AgNO_3$ | 0.28 |

(5) Analysis of Reaction Product

In a 0.1 ml reaction solution, 0.08 units of lactose oxidase and 2.5% of lactose substrate were included. After a reaction for 12 hours, a suitable amount of the reaction product was spotted on a 2×8 cm thin layer chromatography (TLC) plate (silica 60 purchased from Merck), developed with a developing solution consisting of isopropanol and water at a ratio of 4:1, sprayed evenly with 50% sulfuric acid on a thin layer of silica gel, and baked at 150° C.

Figure 4:
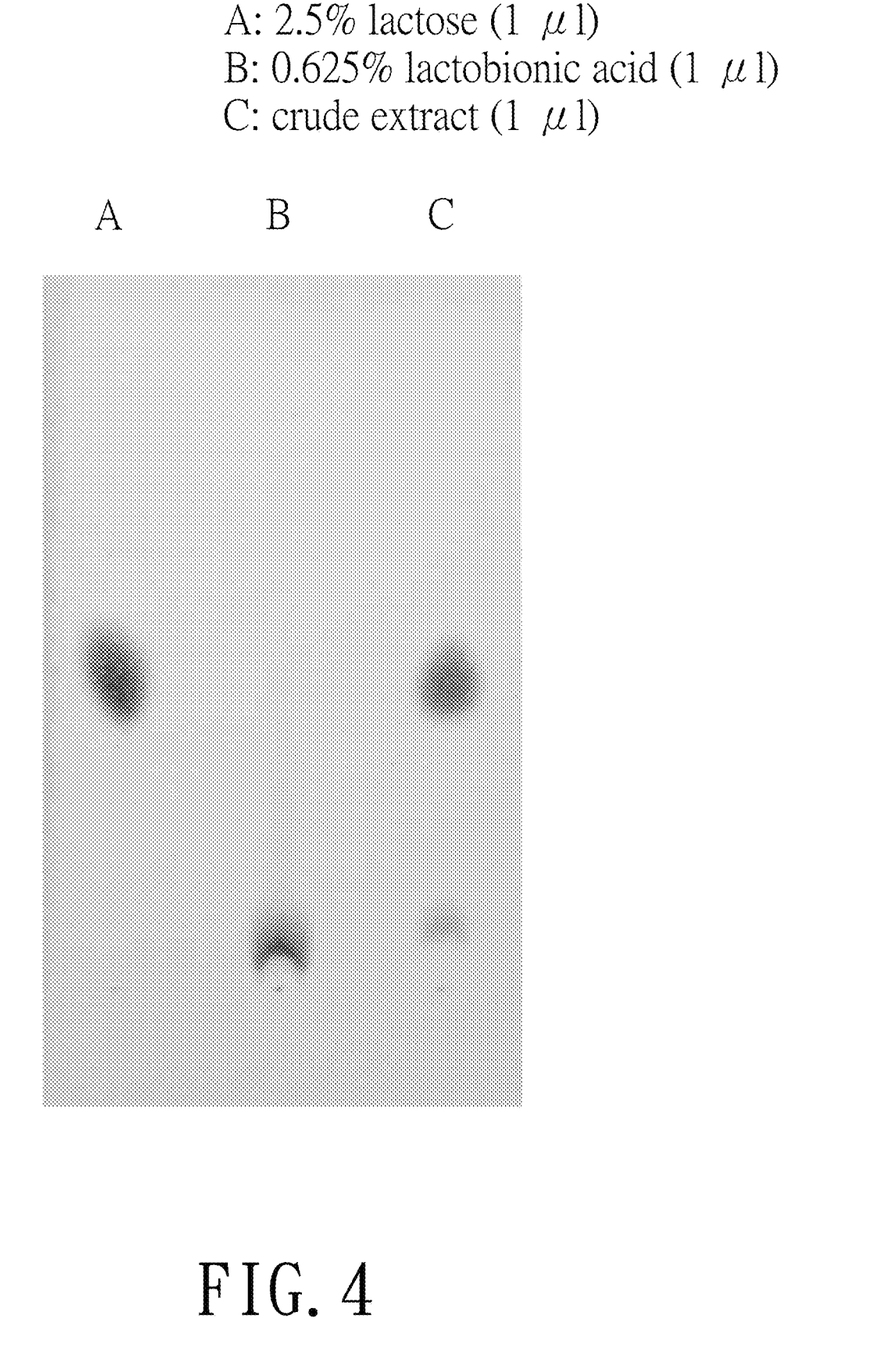
FIG. 4 shows a thin-layer chromatogram of a partial conversion of the lactose into the lactobionic acid by the novel lactose oxidase according to the present invention.
Figure 5:
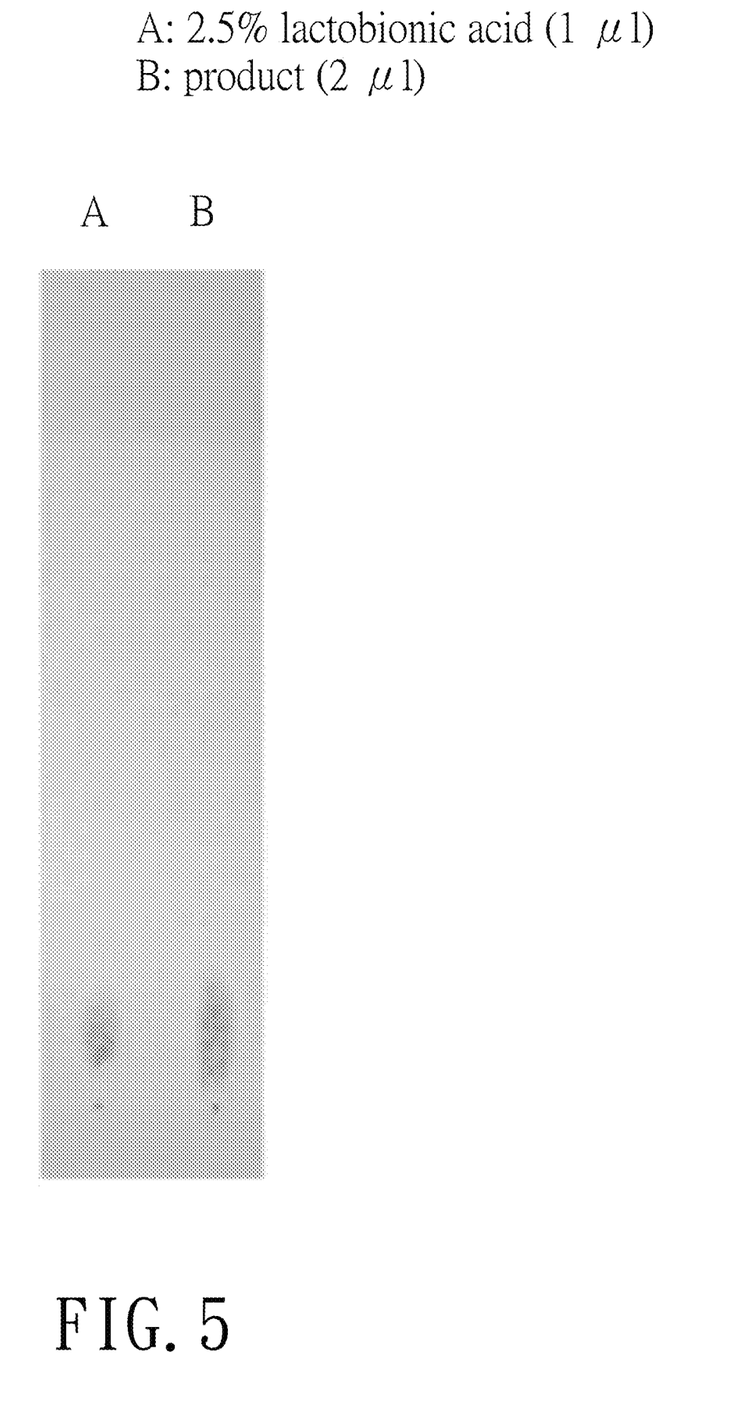
FIG. 5 shows a thin-layer chromatogram of a complete conversion of the lactose into the lactobionic acid by the novel lactose oxidase according to the present invention.

Referring to FIG. 4, the results of TLC were compared with the Rf value. Lane A and Lane B were respectively represented as standards of 2.5% lactose and 0.625% lactobionic acid. The concentration of lactose reactant in crude extract (Lane C) was slightly decreased, but a polar product was obtained. Compared with the lactobionic acid standard, the polar product conforms to the same position as the standard lactobionic acid. Furthermore, as shown in FIG. 5, when the amount of lactose oxidase was increased to 0.6 unit, lactose can be completely converted into lactobionic acid at the same lactose concentration at 16 hours.

Experiment 2: Enzyme Purification (1) Enzyme Purification

A NUK-21 strain was incubated in a MY plate medium at 30° C. for 4 days. Afterwards, 2×2 cm of fungi grown in the plate medium were cut out for inoculation into a 250-ml triangular conical flask containing 5 g of wheat bran and 10 ml of water and cultured at 30° C. for 3-5 days. After the hyphae were covered on the surface of wheat bran, 50 ml of A buffer containing 0.2% SDS was added for enzyme extraction for 20 minutes. The residual wheat bran was filtrated by gauze and centrifuged at 8,500×g for 30 minutes to remove the fungi pellet. The supernatant enzyme solution was obtained, and the enzyme activity was measured.

Ammonium sulfate [$(NH_4)_2SO_4$] precipitation, hydrophobic column Toyopearl phenyl-650M (purchased from TOSOH), HW-50 molecular sieve column (Fractogel HW-50 gel filtration; available from Merck) and Ultrogel-hydroxyapatite column chromatography (purchased from Pall Corporation) were used to obtain a relatively purified enzyme.

Ammonium Sulfate [$(NH_4)_2SO_4$] Precipitation:

After the fungal body was removed from the sample and the sample volume was measured, 55% ammonium sulfate was used for precipitation. The ammonium sulfate input time was about 40 minutes. The entire process was maintained at a low temperature with crushed ice, and the ammonium sulfate was put in the solution and left overnight. Afterwards, centrifuge was conducted to obtain supernatant for further column chromatography.

Hydrophobic Column Toyopearl Phenyl-650M:

The supernatant from the ammonium sulfate precipitation step was passed through a Toyopearl phenyl-650 column (3×25 cm) equilibrated with A buffer containing 55% ammonium sulfate, and then subjected to a gradient of 55%-0% ammonium sulfate to elute the enzymes. Both sides of the gradient maker have a volume of 600 ml, and the operating flow rate is 80 ml per hour.

Sample Concentration:

For molecular sieve column separation, the enzyme must first be concentrated to an appropriate volume. The obtained enzyme solution was added with ammonium sulfate to 55% saturation, then introduced into a small cylinder of Toyopearl phenyl-650 column (2×12 cm) which has been balanced with the same 55%-saturated ammonium sulfate, and directly eluted by A buffer to obtain a concentrated enzyme solution. The operating flow rate was 100 ml per hour.

Fractogel HW-50 Molecular Sieve Column:

The concentrated enzyme solution was passed through a Fractogel HW-50 molecular sieve column (2.5×100 cm) equilibrated with A buffer containing 0.2% SDS, and further flushed by A buffer containing 0.2% SDS. The operating flow rate was 15 ml per hour. The sample was dialyzed with 20-fold volume of 10 mM $K_2HPO_4$—$NaH_2PO_4$ buffer (pH 7.0) for at least 16 hours.

Ultrogel-Hydroxyapatite Column Chromatography:

In order to further purify the enzyme, the Ultrogel-hydroxyapatite column was used, and the enzyme was subjected to buffer exchange. The sample was first dialyzed with 20-fold volume of 10 mM $K_2HPO_4$—$NaH_2PO_4$ buffer (pH 7.0) at 4° C. for at least 16 hours. The enzyme solution collected in the previous step was passed through a Ultrogel-hydroxyapatite column (3×15 cm) equilibrated with 10 mM $K_2HPO_4$—$NaH_2PO_4$ buffer (pH 7.0). The protein that was not adsorbed on the column was washed with 10 mM phosphate buffer, and the then the purified enzyme was eluted by flushing with 10 mM to 400 mM $K_2HPO_4$—$NaH_2PO_4$ buffer. The operating flow rate was 80 ml per hour.

Referring to Table 3, after purification, the specific activity of lactose oxidase increased from 0.7 unit/mg to 5.3 unit/mg. The purification fold was 7.6 times, and the recovery yield was 5.4%.

TABLE 3

Comparison of purification steps of lactose oxidase from the NUK-21 strain

| Steps | Total volume (ml) | Total protein | Total activity (unit) | Specific activity (unit/mg) | Purification fold | Recovery yield (%) |
|---|---|---|---|---|---|---|
| Crude extract | 980 | 418 | 288.2 | 0.7 | 1.0 | 100 |
| Ammonium sulfate precipitation | 1160 | 274 | 281.5 | 1 | 1.4 | 97.7 |
| phenyl-650 M | 378 | 113 | 266.8 | 2.4 | 3.4 | 92.6 |
| HW-50 | 118 | 7.5 | 21.7 | 2.9 | 4.1 | 7.5 |
| Ultrogel-HA | 192 | 2.9 | 15.5 | 5.3 | 7.6 | 5.4 |

(2) Protein Content Determination:

Bradford protein assay (Analytical Biochem, 1976; 72:248-254) method was used in this experiment. In brief, 0.8 ml of different concentrations of bovine serum albumin (2-10 µg) or enzyme samples were placed in test tubes, and 0.2 ml of Bio-Rad Protein Assay reagent was added separately and mixed well for reaction for 10 minutes. The absorbance at OD 595 nm was then determined. After a curve of different concentrations of bovine serum albumin standard protein was determined, the protein concentration of the enzyme sample was calculated by the absorbance of OD 595 nm. The R value was greater than 0.99.

Figure 6:
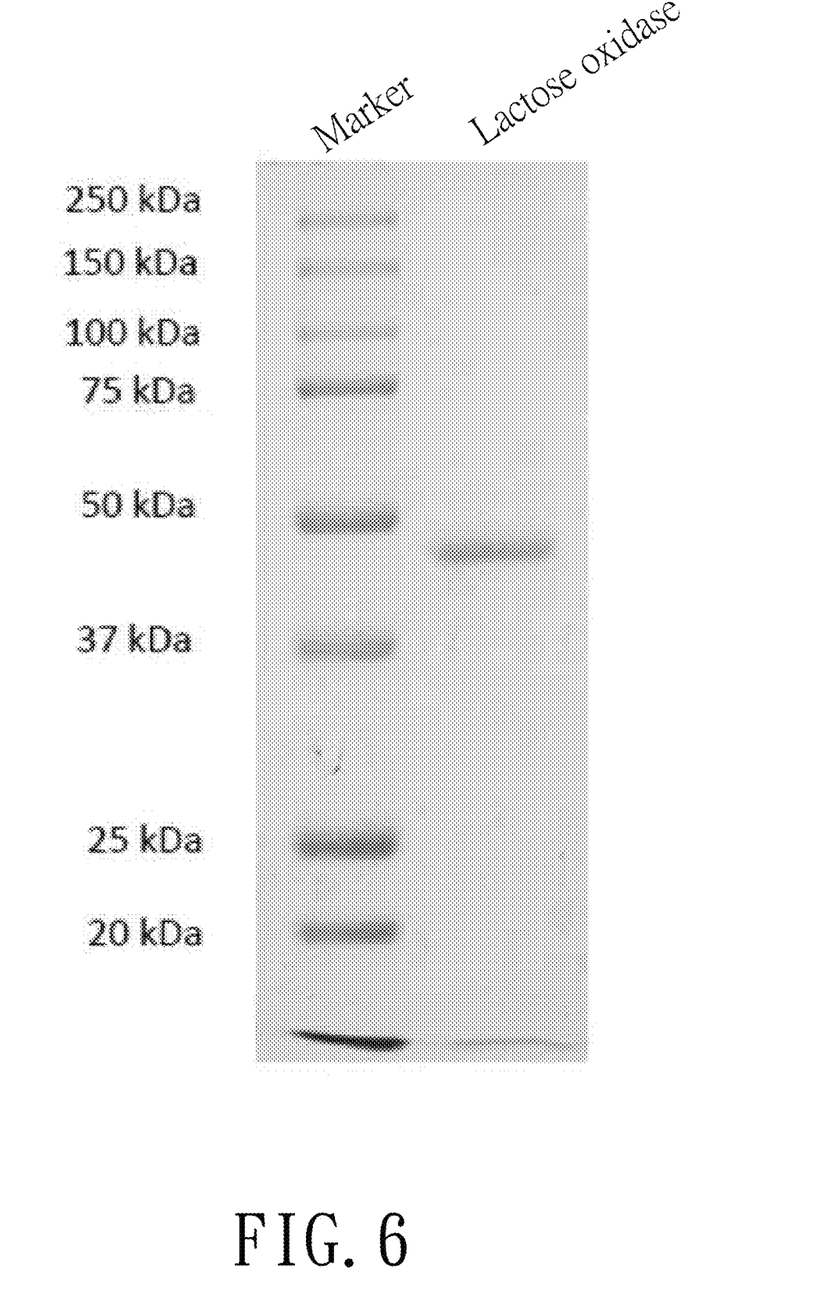
FIG. 6 shows a SDS-PAGE of the novel lactose oxidase according to the present invention.

Experiment 3: Enzyme Characterization (1) Purity and Determination of Molecular Weight by Electrophoresis:

SDS-PAGE was carried out on 10% acrylamide slabs using the modified Laemmli buffer system (Nature 1970; 227:680-5). Coomassie brilliant R-250 was used for staining. The apparent molecular weight of the purified enzyme was 47,200 Da as determined using SDS-PAGE as shown in FIG. 6. Compared with carbohydrate oxidases with similar activity, lactose oxidase has a lower molecular weight.

(2) Prosthetic Group Analysis:

Oxidases usually have a coenzyme to convert or accept electrons. Riboflavins, heme, or metals (such as copper ions) are commonly coenzymes and can be detected by a visible light spectral scan. NUK-21 lactose oxidase did not show any similar signal on the VIS absorption spectrum (data not shown). The content of metals was determined quantitatively by inductively coupled plasma mass spectrometry (ICP-MASS). The enzyme was found to contain 2 mol of Zn/mol of enzyme protein, and its assuming molecule weight was 47.2 kDa.

This was a major discovery that the sugar oxidase contains zinc ion as coenzyme. The $a_{280\ nm}^{1\%}$ value of NUK-21 lactose oxidase was calculated to be 7.58, compared to other oxidases containing colorful coenzyme, which was also consistent with the result that the NUK-21 lactose oxidase do not have signal on the VIS absorption spectrum.

(3) Optimum Reaction pH Test

Fifty mM of various buffers with different pH values were prepared, including $CH_3COOH$—$CH_3COONa$ (pH 4.5-5.5), $K_2HPO_4$—$NaH_2PO_4$ (pH 5.5-8.0), Tris-HCl (pH 7.0-9.0), and $Na_2CO_3$—$NaHCO_3$ (pH 9.0-11). Enzyme activity was determined by peroxidase chromogen method (Clin Chem, 1974; 20:470-475). The substrate, buffer and enzyme were premixed and reacted for 2 minutes, and then 4-aminoantipyrine (4-AA) coloring solution was added for reaction. A spectrophotometer was used to detect the absorbance of $OD_{500\ nm}$ at room temperature (detection at every 15 seconds for a total of 90 seconds). The principle of the 4-AA assay is that the lactose oxidase oxidized lactose to lactobionic acid, which reduces dissolved oxygen to hydrogen peroxide, and the hydrogen peroxide, phenol, and 4-AA were catalyzed by the peroxidase to produce a red quinoneimine structure and show a stable signal at OD 500 nm.

The enzyme activity was defined as the enzyme concentration that produces 1 µmole hydrogen peroxide per minute. Each ml of reaction solution contained 0.7 mM lactose, 0.7 µmol 4-aminoantipyrine, 6 µmol phenol, 3 unit peroxidase, and 30 mM A buffer. Calculation of enzyme activity: unit/ml=$(\Delta A_{500\ nm}/t) \times (Vt/6.8) \times (1/Ve) \times n$, in which $\Delta A_{500\ nm}$: $A_{500\ nm}$ variation in t minutes, 6.8: absorption coefficient of chromogenic material ($mM^{-1}\ cm^{-1}$), Vt: total reaction volume, Ve: volume of enzyme was added, and n: fold of dilution of enzyme solution.

Figure 7:
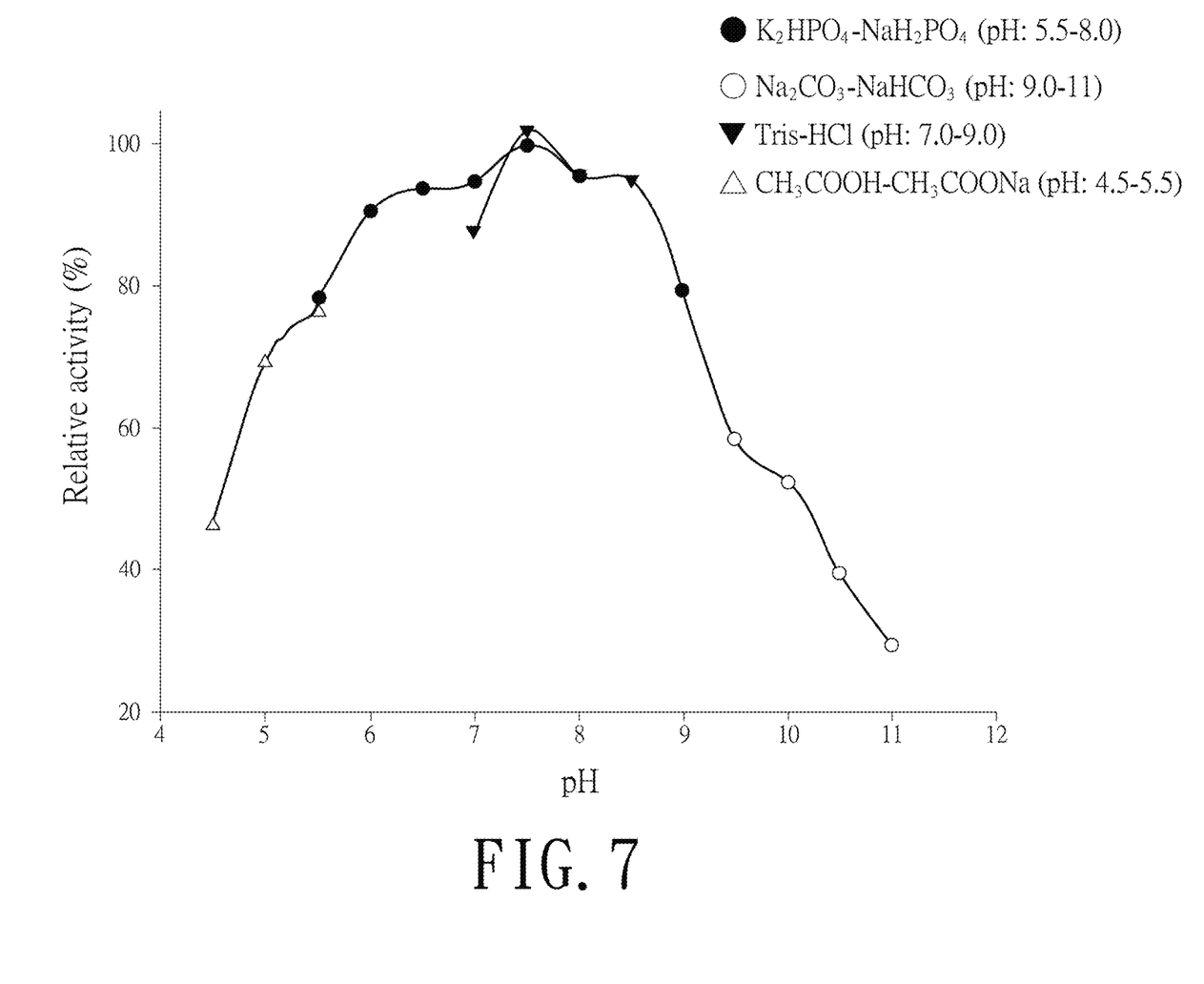
FIG. 7 shows an optimal pH range for reacting the novel lactose oxidase according to the present invention.

Compared with the optimum pH range of pH 4-5 of cellobiose dehydrogenase, pH 5.5 of carbohydrate: acceptor oxidoreductase optimum, and pH 10 of glucooligosaccharide oxidase and cellooligosaccharide oxidase, a preferable pH range for reacting lactose oxidase of the present invention was about 7.5 as shown in FIG. 7, which was near neutral and close to the optimum pH range of catalase. Accordingly, if catalase is used to remove hydrogen peroxide to produce lactobionic acid, it will have advantage for commercial production.

(4) pH Stability Test

Figure 8:
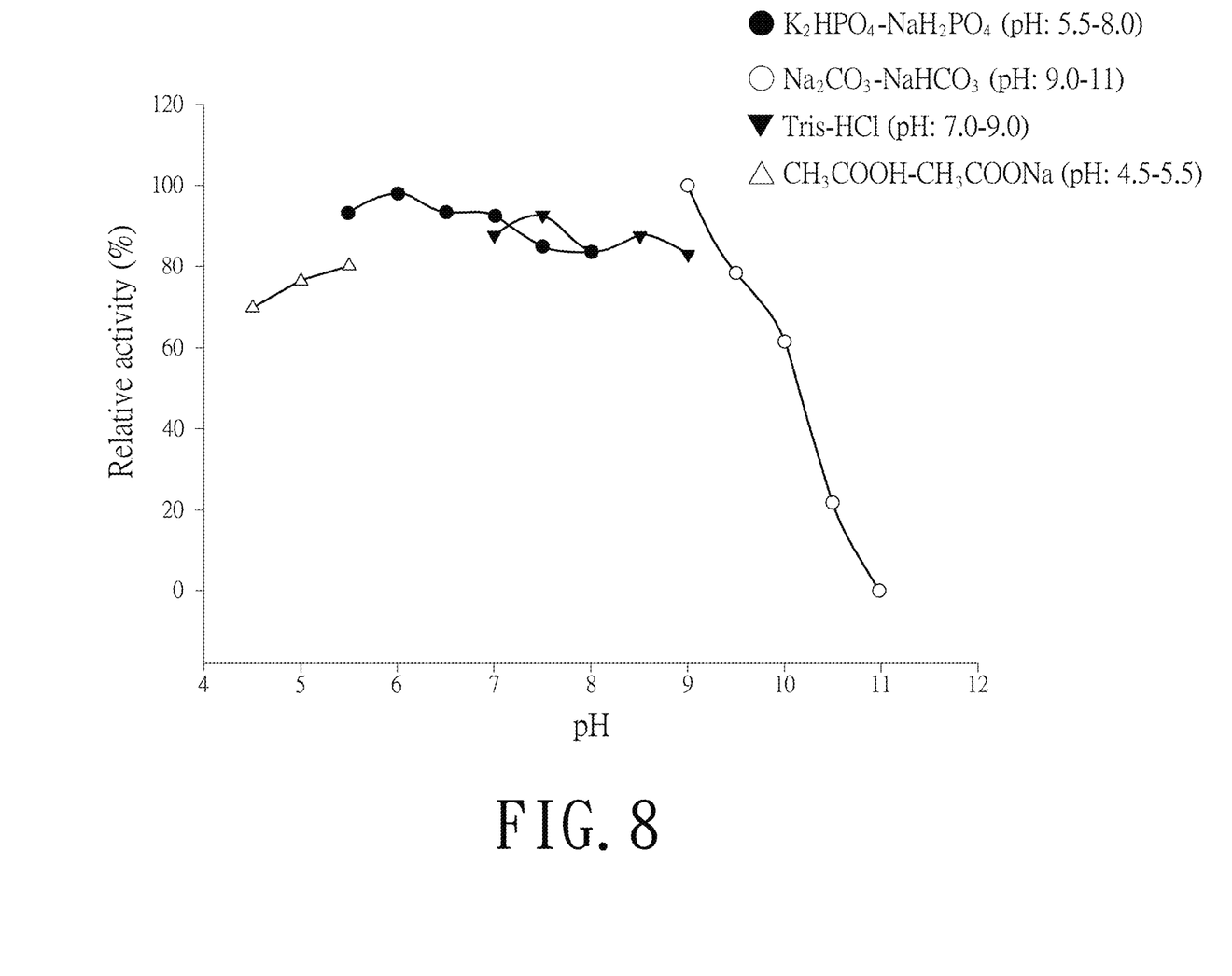
FIG. 8 shows a pH stability of the novel lactose oxidase according to the present invention.

Fifty mM of different buffers with different pH values were prepared. Enzyme and buffer were preliminarily mixed at a ratio of 2:8 and reacted in a water bath at 30° C. for 1 hour. A spectrophotometer was used to detect the absorbance of $OD_{500\ nm}$ at room temperature (detection at every 15 seconds for a total of 90 seconds), and the enzyme activity was determined. Referring to FIG. 8, the lactose oxidase retained an enzyme activity of more than 80% after a stability test at pH 5.5-9 for one hour.

(5) Optimal Reaction Temperature Test

Figure 9:
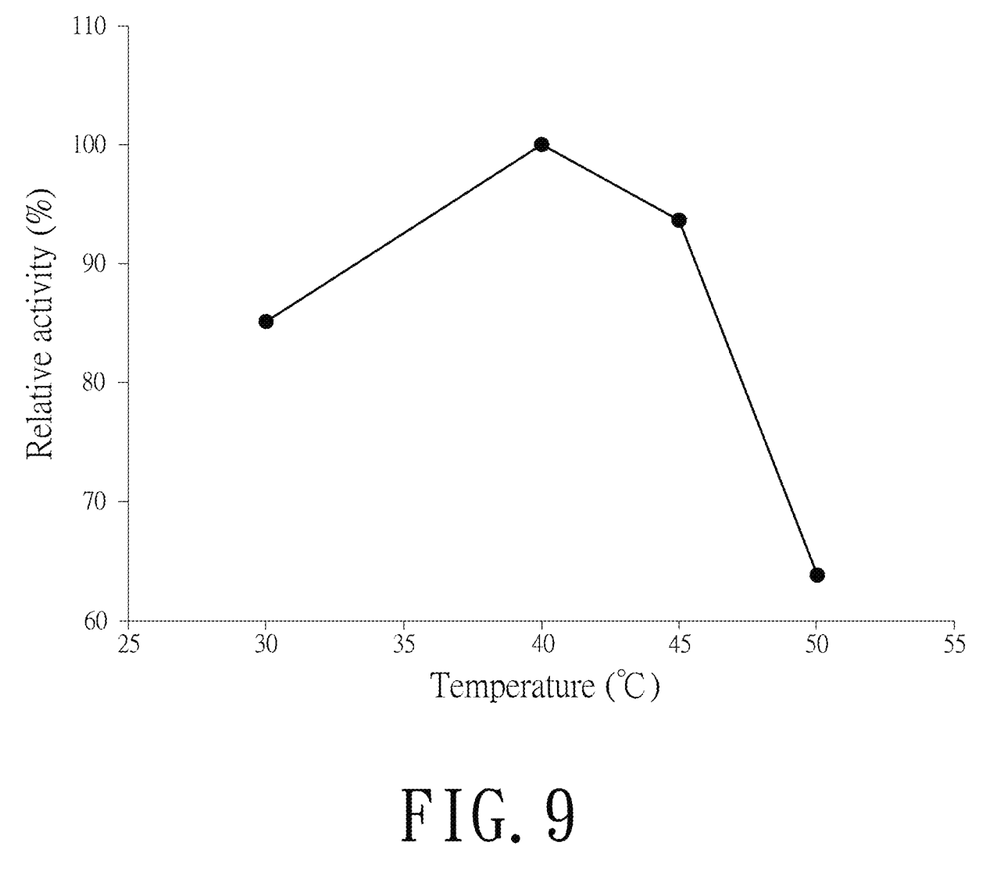
FIG. 9 shows an optimal temperature range for reacting the novel lactose oxidase according to the present invention.

Dissolved oxygen assay was used to determine the enzyme activity of lactose oxidase at different reaction temperatures. According to the characteristics of oxygen consumption by the enzyme reaction, the rate of oxygen decline during enzyme reaction can be detected by the dissolved oxygen electrode (HQ 430d/HACH, USA). A 5 ml reaction tank was added with 4.85 ml of A buffer containing 0.7 mM lactose for equilibration at 30° C. for 5 minutes, and then the solution was added with appropriate amount of enzyme to observe the change of oxygen consumption on the recorder. Referring to FIG. 9, it was found that the lactose oxidase has the highest activity at a temperature of 40° C. and 85% activity at 30° C.

(6) Temperature Stability Test

Figure 10:
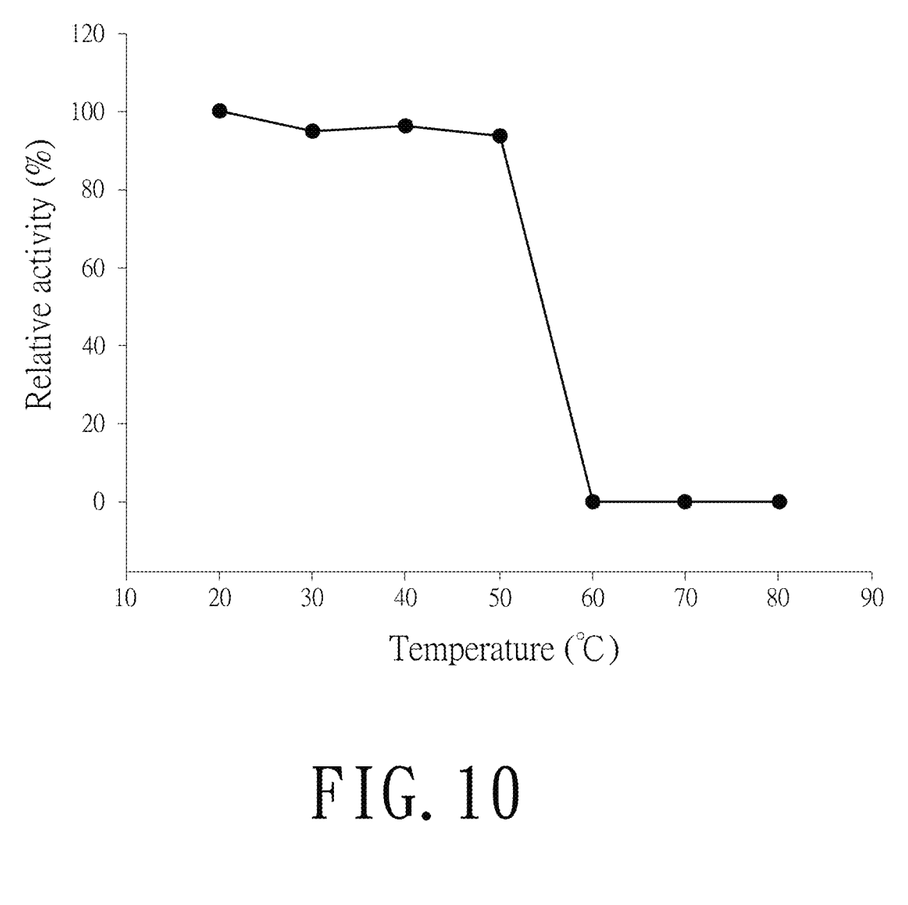
FIG. 10 shows a temperature stability of the novel lactose oxidase according to the present invention.

Enzyme and buffer were mixed at a ratio of 2:8 and reacted in a water bath at different temperatures for 1 hour. A spectrophotometer was used to detect the absorbance of $OD_{500\ nm}$ at room temperature (detection at every 15 seconds for a total of 90 seconds), and the enzyme activity was determined. Referring to FIG. 10, lactose oxidase retained more than 90% activity at a temperature ranging from 20° C. to 50° C. for 1 hour, but the lactose oxidase almost lost its activity at 60° C. or more.

(7) Substrate Specificity

A spectrophotometer was used to detect the absorbance of $OD_{500\,nm}$ at room temperature (detection at every 15 seconds for a total of 90 seconds), and the enzyme activity was determined. Referring to Table 4, at a low concentration (0.7 mM) of monosaccharide and disaccharide substrates, the relative activities of the lactose oxidase of the present invention were 100%, 83.4%, and 4.1% for lactose, cellobiose, and maltose, respectively. At a high concentration (7 mM) of substrates, the performance of relative activity of the lactose oxidase was also approximately the same as that of the low concentration.

TABLE 4

Substrate specificities to the lactose oxidase of the NUK-21 strain

| | | Relative activity (%) | |
|---|---|---|---|
| Substrate | Bonding type | 0.7 mM Substrate | 7 mM Substrate |
| Lactose | Gal-Glu, β 1→4 | 100 | 100 |
| Cellobiose | Glu-Glu, β 1→4 | 83.4 | 81.7 |
| Maltose | Glu-Glu, α 1→4 | 4.1 | 24.8 |
| Sucrose | Glu-Fru, α 1→2 | 0 | 0 |
| lactobionic acid | Gal-Glu, β 1→4 | 0 | 0 |
| Galactose | — | 0 | 1.8 |
| Glucose | — | 0 | 9.2 |
| Fructose | — | 0 | 0 |
| Xylose | — | 0 | 0 |
| Xylitol | — | 0 | 0 |
| Sorbitol | — | 0 | 0 |

Referring to Table 5, compared with other published carbohydrate oxidases, the specificity to disaccharides, especially to cellobiose, was higher than that of lactose, but the specificity of lactose oxidase of the present invention to lactose was higher than that of cellobiose. The Kin values of lactose oxidase for lactose, cellobiose, and maltose were 0.076 mM, 0.063 mM, and 21.74 mM, respectively (not shown in the Table 5). Obviously, the lactose oxidase had a better affinity for cellobiose and lactose. The Kcat values of lactose oxidase for lactose, cellobiose, and maltose were 97.1 $S^{-1}$, 71.5 $S^{-1}$, and 65.6 $S^{-1}$ (not shown in the Table 5). It can be seen that the Kcat value of the lactose oxidase of the present invention is the best in the currently published literature.

TABLE 5

Comparison of kinetic parameters of carbohydrate oxidases from different strains

| | | Km (mM) | | Substrate specificity (%) | |
|---|---|---|---|---|---|
| Enzyme | Strain | Lactose | Cellobiose | Lactose | Cellobiose |
| Lactose oxidase | *Myrmecridium flexuosum* NUK-21 | 0.076 | 0.063 | 100 | 83.4 |
| Cellobiose dehydrogenase | *Sporotrichum pulverulentum* | — | — | 100 | 162 |
| Cellobiose oxidase | *Sporotrichum pulverulentum* | 0.58 | 0.042 | — | — |
| Carbohydrate: acceptor oxidoreductase | *Paraconiothyrium* sp. | 0.11 | 0.13 | — | — |
| Carbohydrate: acceptor oxidoreductase (Novo) | *Microdochium nivale* | 0.066 | — | 52 | 100 |
| Glucooligosaccharide oxidase | *Acremonium strictum* | 0.38 | 0.12 | 100 | 120 |
| Cellooligosaccharide oxidase | *Sarocladium oryzae* | 2.7 | 19.8 | 83 | 100 |

(8) Effects of Metal Ions on Enzyme Activity

The purified enzyme was added to A buffer containing 1 mM of different metal solution and incubated in a water bath at 30° C. for 1 hour. Dissolved oxygen assay was used to determine the enzyme activity of lactose oxidase at different reaction temperatures. According to the characteristics of oxygen consumption by the enzyme reaction, the rate of oxygen decline during enzyme reaction can be detected by the dissolved oxygen electrode (HQ 430d/HACH, USA). A 5 ml reaction tank was added with 4.85 ml of A buffer, appropriate amount of enzyme, and 1 mM metal solution for reaction at 30° C. for 1 hour, and then 0.7 mM lactose was added to the solution to observe the change of oxygen consumption on the recorder.

Referring to Table 6, most of the metal ions had little effect on the lactobionic acid activity, but $Fe^{2+}$ and $Sn^{2+}$ inhibited the enzyme activities which were decreased to 61.3% and 89.7%, respectively. The lactobionic acid activity was increased by $Hg^{2+}$ to 153.8%. For most enzymes, $Hg^{2+}$ is usually inhibitor. However, the lactose oxidase activity of the present invention increased by about 50% under the influence of $Hg^{2+}$.

TABLE 6

Effect of metal ions on lactose oxidase activity of the NUK-21 strain

| Metal ions (1 mM) | Relative activity (%) |
|---|---|
| Control group | 100 |
| $AgNO_3$ | 107.9 |
| $CaCl_2$ | 109.5 |
| $CdSO_4$ | 100 |
| $CoCl_2$ | 110.2 |
| $CuSO_4$ | 96.8 |
| $FeSO_4$ | 61.1 |
| $FeCl_3$ | 103.2 |
| $HgCl_2$ | 153.8 |

TABLE 6-continued

Effect of metal ions on lactose oxidase
activity of the NUK-21 strain

| Metal ions (1 mM) | Relative activity (%) |
|---|---|
| NiSO$_4$ | 100 |
| PbCl$_2$ | 89.7 |
| SnCl$_2$ | 61.3 |

(9) Effects of Chemicals on Enzyme Activity

The purified enzyme was added to A buffer containing 1 mM of various chemical solution and incubated in a water bath at 30° C. for 1 hour. Dissolved oxygen assay was used to determine the enzyme activity of lactose oxidase. Referring to Table 7, the enzyme activity was activated by N-ethylmaleimide, EDTA and NaN$_3$. Only 2-bromo-4'-nitroacetophenol had a significant inhibitory effect on lactose oxidase. 2-bromo-4'-nitroacetophenol, the most potent inhibitor among histidine group-modifying reagent, inhibited the enzyme activity competitively with respect to the substrate lactose. The inhibition constant (Ki) for 2-bromo-4'-nitroacetophenol was found to be 0.086 mM, which is similar to the Km value of lactose oxidase for lactose found to be 0.076 mM. It is considered that 2-bromo-4'-nitroacetophenol showed the non-competitive inhibition to the enzyme reaction by blocking the histidine involved in the enzymes.

TABLE 7

Effect of chemicals on lactose oxidase
activity of the NUK-21 strain

| Chemicals (1 mM) | Concentration (mM) | Relative activity (%) |
|---|---|---|
| Control group | 1 | 100 |
| 2,4'-dibromoacetophenone | 1 | 99 |
| 2-bromo-4'-nitroacetophenol | 1 | 87.8 |
| NaN$_3$ | 1 | 131.3 |
| EDTA | 1 | 136.3 |

TABLE 7-continued

Effect of chemicals on lactose oxidase
activity of the NUK-21 strain

| Chemicals (1 mM) | Concentration (mM) | Relative activity (%) |
|---|---|---|
| N-ethylmaleimide | 1 | 139.5 |
| 1,10-phenanthroline | 1 | 98.8 |
| H$_2$O$_2$ | 1 | 100 |
| PMSF | 1 | 104.9 |
| 2-bromo-4'-nitroacetophenol | 4 | 53 |

Experiment 4: Production of Lactobionic Acid

Figure 11:
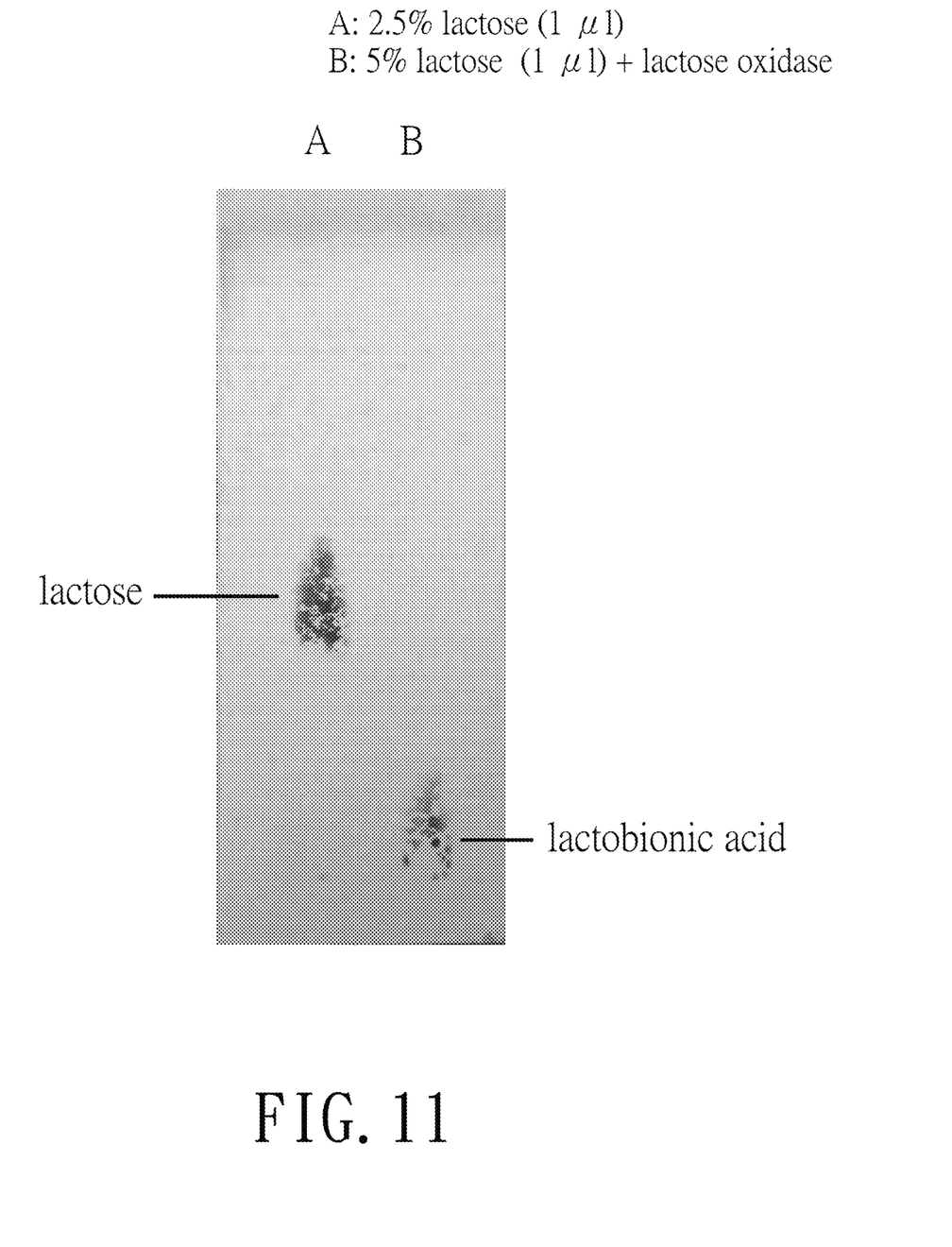
FIG. 11 shows a thin-layer chromatogram of mass production of the lactobionic acid.

A 100 ml of reaction solution consisting of 50 mM Tris-HCl buffer (pH 7.5), 50 units of lactose oxidase, 2.5% lactose, and 400 units of catalase was prepared and mixed at 28° C. on a rotary shaker at 400 rpm. In the reaction, 1N NaOH was used for titration to maintain pH at 7.5. The reactants were then analyzed by silica thin layer chromatography. After a reaction for 10 hours, lactose was completely converted to lactobionic acid as shown in FIG. 11.

Compared with the technique available now, the present invention has the following advantages:

1. The *Myrmecridium flexuosum* NUK-21 of the present invention produces a novel lactose oxidase which can be used to convert lactose into lactobionic acid and has a high yielding rate, e.g. NUK-21 cultured in a medium containing 5 g wheat brans producing more than 25 units of lactose oxidase.

2. The novel lactose oxidase of the present invention has a high substrate specificity (Km 0.076 mM, and K$_{cat}$ 97.1 s$^{-1}$) and an excellent stability at a temperature ranging from 25° C. to 50° C. and a pH value ranging from 5.5 to 9.

3. The novel lactose oxidase of the present invention has a high lactose conversion rate of 100%, so it can completely converse lactose into lactobionic acid in a short period of time of about 10 hours, which significantly reduces production costs and is suitable for industrial mass production in practical applications.

What is claimed is:

1. A method of producing a cultured lactose oxidase from an isolated and purified *Myrmecridium flexuosum* NUK-21, deposited under the DSMZ deposit accession number DSM 32781.

2. The method of claim 1, wherein said cultured lactose oxidase has a molecular weight of 47.2 kDa, a catalytic reaction rate for lactose (Kin) of 0.076 mM, a catalyst rate constant ($K_{cat}$) of 97.1 $s^{-1}$ and a conversion rate of 100% for lactose.

3. A process of preparing a cultured composition containing a lactose oxidase for conversion of lactose into lactobionic acid, comprising:
    (a) inoculating a culturing medium with the isolated and purified *Myrmecridium flexuosum* NUK-21 deposited under the DSMZ deposit accession number DSM 32781; and
    (b) culturing the isolated and purified *Myrmecridium flexuosum* NUK-21 at a temperature of 25° C. to 35° C. for 3 to 7 days.

4. The method as claimed in claim 3, wherein the culturing medium is selected from a solid medium containing wheat bran and water, a liquid medium containing wheat bran, sodium chloride (NaCl) and cupric ions ($Cu^{2+}$), or a liquid medium containing defatted soybean flours.

5. A method for conversion of lactose into lactobionic acid by a lactose oxidase, comprising inoculating a culturing medium with the isolated and purified *Myrmecridium flexuosum* NUK-21 deposited under the DSMZ deposit accession number DSM 32781, and culturing the isolated and purified *Myrmecridium flexuosum* NUK-21 under a culturing condition to convert lactose into lactobionic acid, wherein the culturing medium is selected from a solid medium containing wheat bran and water, a liquid medium containing wheat bran, sodium chloride (NaCl) and cupric ions ($Cu^{2+}$), or a liquid medium containing defatted soybean flours.

6. The method for conversion of lactose into lactobionic acid by a lactose oxidase as claimed in claim 5, wherein the solid medium in which the isolated and purified *Myrmecridium flexuosum* NUK-21 is cultured for 3.5 days has an enzyme activity of 6 units/g, and the liquid medium in which the isolated and purified *Myrmecridium flexuosum* NUK-21 is cultured for 4 days has an enzyme activity of 0.55 unit/ml.

* * * * *